United States Patent
Kiselev

(10) Patent No.: US 9,393,230 B2
(45) Date of Patent: Jul. 19, 2016

(54) PHARMACEUTICAL COMPOSITION ON THE BASIS OF PHYTO-NUTRIENTS WITH INCREASED BIOAVAILABILITY, HAVING ANTI-TUMOR ACTIVITY, AND METHOD FOR PRODUCING SAID COMPOSITION (ALTERNATIVES)

(71) Applicant: Nordic Labs Limited, Newhouse, Lanarkshire (GB)

(72) Inventor: Vsevolod Ivanovich Kiselev, Moscow (RU)

(73) Assignee: Nordic Labs Limited, Newhouse, Lanarkshire (GB)

( * ) Notice: Subject to any disclaimer, the term of this patent is extended or adjusted under 35 U.S.C. 154(b) by 0 days.

(21) Appl. No.: 14/435,846

(22) PCT Filed: Jul. 19, 2013

(86) PCT No.: PCT/RU2013/000568
§ 371 (c)(1),
(2) Date: Apr. 15, 2015

(87) PCT Pub. No.: WO2014/062083
PCT Pub. Date: Apr. 24, 2014

(65) Prior Publication Data
US 2015/0265575 A1 Sep. 24, 2015

(30) Foreign Application Priority Data
Oct. 16, 2012 (RU) .................................. 2012144002

(51) Int. Cl.
*A61K 31/404* (2006.01)
*A61K 31/121* (2006.01)
*A61K 31/353* (2006.01)
*A61K 31/05* (2006.01)
*A61K 31/352* (2006.01)
*A61K 9/14* (2006.01)
*A61K 9/00* (2006.01)

(52) U.S. Cl.
CPC ............. *A61K 31/404* (2013.01); *A61K 9/0053* (2013.01); *A61K 9/146* (2013.01); *A61K 31/05* (2013.01); *A61K 31/121* (2013.01); *A61K 31/352* (2013.01); *A61K 31/353* (2013.01)

(58) Field of Classification Search
None
See application file for complete search history.

(56) References Cited

U.S. PATENT DOCUMENTS

| 2012/0201865 A1* | 8/2012 | Dorairaju | A23K 1/003 424/400 |
| 2014/0303225 A1 | 10/2014 | Kiselev et al. | |

FOREIGN PATENT DOCUMENTS

| RU | 2 409 363 C1 | 1/2011 |
| RU | 2 456 987 C1 | 7/2012 |
| WO | 2007/103435 A2 | 9/2007 |
| WO | 2012/049253 A1 | 4/2012 |

OTHER PUBLICATIONS

International Search Report of PCT/RU2013/000568, mailed Dec. 12, 2013.

* cited by examiner

*Primary Examiner* — Yevegeny Valenrod
(74) *Attorney, Agent, or Firm* — Collard & Roe, P.C.

(57) ABSTRACT

A pharmaceutical composition for peroral delivery of phyto-nutrients includes at least one phyto-nutrient from the following series: epigallocatechin-3-gallate, diindolylmethane, genestein, resveratrol, curcumine, and a solubilizer—a polyvinylcaprolactam/polyvinylacetate/polyethyleneglycol graft copolymer with an average molecular mass of 90000-140000 g/mol at a mass ratio of at least one phyto-nutrient and solubilizer of 1/5 to 1/1. The composition can additionally include a pharmaceutically acceptable carrier. The composition may be produced by dissolving the solubilizer in an organic solvent, dissolving at least one phyto-nutrient in the same organic solvent, mixing the resulting solutions, and distilling off the solvent in vacuo. The resulting mixture is heated to 45-50° C. with constant stirring and, after distillation, the product is dried in vacuo. Ethanol, acetone, or isopropanol can be used as the organic solvent. Alternatively, the composition may be produced by dry mixing the powders of the solubilizer and of at least one phyto-nutrient.

3 Claims, 9 Drawing Sheets

PHARMACEUTICAL COMPOSITION ON THE BASIS OF PHYTO-NUTRIENTS WITH INCREASED BIOAVAILABILITY, HAVING ANTI-TUMOR ACTIVITY, AND METHOD FOR PRODUCING SAID COMPOSITION (ALTERNATIVES)

CROSS REFERENCE TO RELATED APPLICATIONS

This application is the National Stage of PCT/RU2013/000568 filed on Jul. 19, 2013, which claims priority under 35 U.S.C. §119 of Russian Application No. 2012144002 filed on Oct. 16, 2012, the disclosures of which are incorporated by reference. The international application under PCT article 21(2) was not published in English.

The present invention relates to the field of pharmacy and concerns novel pharmaceutical compositions for peroral delivery of phyto-nutrients having anti-tumor activity.

The part of compositions of vegetable origin in the creation of novel medicinal preparations arouses an unprecedented interest in the last years. This problem has given rise to many studies resulting in the detection of a series of compounds showing a wide range of biological activities, such as flavonoids, flavins, catechins, etc. (John Boik (2012) Natural Compounds in Cancer Therapy, book, 521).

The highest interest is aroused by the phyto-nutrients as follows: diindolylmethane (that is an indole of plants found in cruciferous vegetables such as broccoli, Brussels sprouts and cauliflower; the chemical formula of the compound is $C_{17}H_{14}N_2$), epigallolcatechol-3-gallat (it is a variety of cathechin, contained in tea at high amounts; the formula of the compound is $C_{22}H_{18}O_{11}$), genistein (an isoflavone that is a natural component obtainable from such a source as soya; the compound formula is $C_{15}H_{10}O_5$), resveratrol (a natural phyto-alexin contained in the rind of red grapes and of some other berries and plants that is released by the last as a protecting reaction against parasites such as bacteria or fungi; the compound formula is $C_{14}H_{12}O_3$), curcumin (it represents the main curcuminoid making part of turmeric root, dimethoxycurcumin and bis-dimethoxycurcumin being related to the curcuminoids as well; the compound formula is $C_{21}H_{20}O_6$).

It has been established that these compounds of vegetable origin inhibit the proliferation of tumor cell lines of various genesis in vitro. The maximal effects are observed in the range of 5 to 50 micromoles. Such concentrations cannot be achieved while taking these compounds with food. Attempts to reproduce the anti-tumor activity of these substances in vivo are not always successful.

A detailed study of the molecular mechanisms of the anti-tumor effect has shown that these substances inhibit multiple signal cascades controlling the tumor growth and metastasis spreading. They regenerate the apoptotic properties of transformed cells, which results in a natural death of the same via the mechanism of programmed death. Antiangiogeny properties of these substances have been studied in detail to show their substantial contribution to their anti-tumor effect consisting in the inhibition of the growth of new vessels in a growing tumor.

Recently, the ability of some phyto-nutrients to selectively inhibit the viability of tumor stem cells has been described. This unique ability seems to be due to the effect on embryo signal cascades. It was established that this class of compounds increases the sensitivity of tumors to the effect of cytostatics and prevents the development of radioresistance originating in the course of radial therapy. Thus, there are no doubts about a huge therapeutic potential of phyto-nutrients (Fazlul H. Sarkar, Yiwei Li, Zhiwei Wang and Dejuan Kong (2009), Cellular signaling perturbation by natural products, *Cell Signal,* 21(11), 1541-1547; Sanjeev Banerjee, Dejuan Kong, Zhiwei Wang, Bin Bao, Gilda G. Hillman, Fazlul H. Sarkar (2011), Attenuation of multi-targeted proliferation-linked signaling by 3,30-diindolylmethane (DIM): From bench to clinic, *Mutation Research,* 728(1-2), 47-66). Any active practical introduction of medicinal products on their base is forbidden, according to a general point of view, by their low bioavailability. It was established, for many of them, that even at high dosages of phyto-nutrients coming up to some grams and administered orally, no efficient concentrations can be attained in blood and in targeted organs.

For solving this problem, important efforts have been made and various approaches have been developed. It is known the use of pluronics for improving the bioavailability of genistein (Suk Hyung Kwon, Sun Young Kim, Kyoung Wook Ha et al. (2007), Pharmaceutical Evaluation of Genistein-loaded Pluronic Micelles for Oral Delivery, *Arch Pharm Res,* 30(9), 1138-1143). Search for new formulations for other phyto-nutrients is in progress (Imtiaz A. Siddiqui, Vaqar M. Adhami, Nihal Ahmad and Hasan Mukhtar (2010), Nanochemoprevention, *Nutr Cancer,* 62(7), 883-890; Lu Y, Ding N, Yang C, Huang L, Liu J, Xiang G. (2012). Preparation and in vitro evaluation of a folate-linked liposomal curcumin formulation, *Liposome Research,* 22(2), 110-119).

The authors of the present invention have developed new technological solutions enabling to improve the bioavailability of diindolylmethane (DIM) and of epigallocatechol-3-gallate (EGCG). The pharmaceutical compositions for peroral delivery of diindolylmethane and the process of producing the same described in the RF patent No 2409363 are the closest prior art to the present invention.

The pharmaceutical composition for peroral administration comprises 3,3-diindolylmethane (DIM) as the main component and a specific additive representing an oxyethylene-oxypropylene block copolymer, in which the content of hydrophobic block is less than 50 mass percent and the molecular mass of the hydrophilic block is 2250 Da and more, for the ratio of the active component and the selected block copolymer of 10:1 to 2:1. As the oxyethylene-oxypropylene block copolymer, the composition can preferably contain Pluronic F127, it can additionally contain Pluronic L10 as well as a pharmaceutically acceptable carrier. One of the possible processes for producing said pharmaceutical composition comprises dissolving Pluronic F127 in ethanol, dissolving DIM in ethanol, mixing said solutions, treating the same with ultrasound, eliminating ethanol in a rotary dissolving apparatus or a "SpeedVac" concentrator, and evaporating under vacuum.

Application of different approaches to solve the problem of the DIM bioavailability improvement showed that every compound requires an individual solution. In particular, the use of pluronics while dealing with DIM enables one not only to substantially increase the bioavailability but to develop as well an industrial technology for producing the DIM substance under a novel, bioavailable formulation. A similar approach used while dealing with EGCG improved somewhat the bioavailability of the substance but did not enable to solve the problem of its high-volume production. The use of pluronics to obtain bioavailable compositions on the basis of the examples of other phyto-nutrients, in particular of green tea catechins, neither enabled to develop an industrial technology for producing said preparation.

It is necessary to observe that the combination of these substances leads to a well-expressed synergetic effect. It means that the production of combined preparations on the basis of phyto-nutrients opens additional possibilities for their use in clinical practice. For this reason, universal technological solutions are required to enable an improved bioavailability of these compounds, to enable production of combined preparations containing two or more compounds that could satisfy the requirements imposed to pharmaceutical technologies under the conditions of an industrial production.

The purpose of the present invention is to enlarge the range of pharmaceutical compositions based on phyto-nutrients and the range of the processes for their production, in particular for obtaining novel nanomicellar structures containing phyto-nutrients and providing for a high bioavailability at peroral administration, as well as a high stability in storage.

This task is resolved by the fact that in a pharmaceutical composition for peroral administration, having anti-tumor activity, comprising at least one phyto-nutrient and a solubilizer, according to the present invention, at least one phyto-nutrient from the following series: epigallocatechol-3-gallate, diindolylmethane, genistein, resveratrol, curcumin, and as a solubilizer, the composition comprises a polyvinylcaprolactam/polyvinylacetate/polyethyleneglycol graft copolymer with an average molecular mass of 90000-140000 g/mol at a mass ratio of at least one phyto-nutrient and of the solubilizer of 1:5 to 1:1.

Furthermore, the composition can additionally comprise a pharmaceutically acceptable carrier. The above given task is resolved as well by a method for producing the pharmaceutical composition for peroral administration (according to the first embodiment), having anti-tumor activity, consisting in that the solubilizer is dissolved in an organic solvent, at least one phyto-nutrient is dissolved in the same organic solvent, the resulting solutions are mixed and the solvent is distilled off in vacuum, wherein, according to the present invention, use is made of at least one phyto-nutrient selected from the following series: epigallocatechol-3-gallate, diindolylmethane, genistein, resveratrol, curcumin, and as a solubilizer, use is made of a polyvinylcaprolactam/polyvinylacetate/polyethyleneglycol graft copolymer with an average molecular mass of 90000-140000 g/mol at a mass ratio of at least one phyto-nutrient and of the solubilizer of 1:5 to 1:1, after mixing the solutions, the resulting mixture is heated to 45-50° C. with constant stirring, and after distillation, the product is dried in vacuum.

Furthermore, ethanol or acetone or isopropanol can be used as the organic solvent.

Furthermore, after drying, a pharmaceutically acceptable carrier can be introduced into the product obtained.

Said task is resolved as well by a method for producing a pharmaceutical composition for peroral administration (according to the second embodiment), consisting in the mixing of a powdered solubilizer in the capacity of which a polyvinylcaprolactam/polyvinylacetate/polyethyleneglycol graft copolymer with an average molecular mass of 90000-140000 g/mol is taken, with a powder of at least one phyto-nutrient taken from the following series: epigallocatechol-3-gallate, diindolylmethane, genistein, resveratrol, curcumin, at a mass ratio of at least one phyto-nutrient and of the solubilizer of 1:1 to 1:5, the mixture being stirred until obtaining a homogeneous powder.

The polyvinylcaprolactam/polyvinylacetate/polyethyleneglycol graft copolymer is produced in particular by the BASF company under the trade name Soluplus® and has the formula:

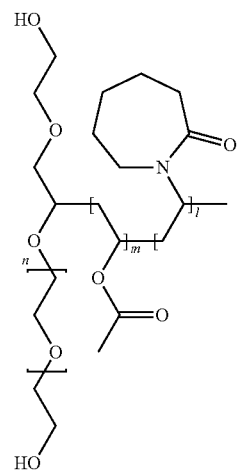

The copolymer has the ability to form "solid solutions" with difficultly soluble active ingredients of medicinal preparations which improves the assimilability of the same by a human organism. It was developed in 2007, and in 2009, it was presented to public for the first time as an innovative filler.

The product according to the present invention is developed especially for a modern method for producing medicines by extrusion from a molten mass. This technology gets an increasingly wide spreading for enabling one to create technologies of producing finished dosage forms with medicines characterized by a low solubility and a low absorbability from the gastrointestinal tract. The essence of the method consists in the following operations: individual components of a medicine are placed into an extruder, mixed and molten at a high temperature, which is followed by addition of the polymeric product "Soluplus®. When so doing, active pharmaceutical ingredients are dissolved in the polymer thus forming so called "solid solutions". As a result, the medicines that are characterized by their low biological availability in the use of other variants of finished dosage forms are much better assimilated by a human organism while delivered with a new base for finished medicines (http://www.pharma-ingedients.basf.com/Documents//ENP/Poster/EN/GNOMD387.pdf).

The phyto-nutrients representing active substances according to the present invention have a different solubility; for example, epigallo-3-catechin is water-soluble while curcumin is not practically water-soluble. The problem consists in that all of them do not endure high temperatures, that is why it is not possible to prepare their medicinal dosage forms by the known method.

We have unexpectedly established that if phyto-nutrients are submitted to a process of molecular codispergation with a polymer component in a selected cosolvent chosen from the group of ethanol, isopropanol, acetone, followed by drying, a stable pharmaceutical composition with increased bioavailability can be obtained. It gives a solid water-soluble product that forms, while mixed with a water-containing agent, colloidal micelles that are better assimilated by a human organism.

It is possible to introduce 20 to 50% (depending on the nature of a substance) of active pharmaceutical agent such as epigallocatechol-3-gallate, diindolylmethane, genistein, resveratrol, curcumin, or their mixtures.

Figure 1:
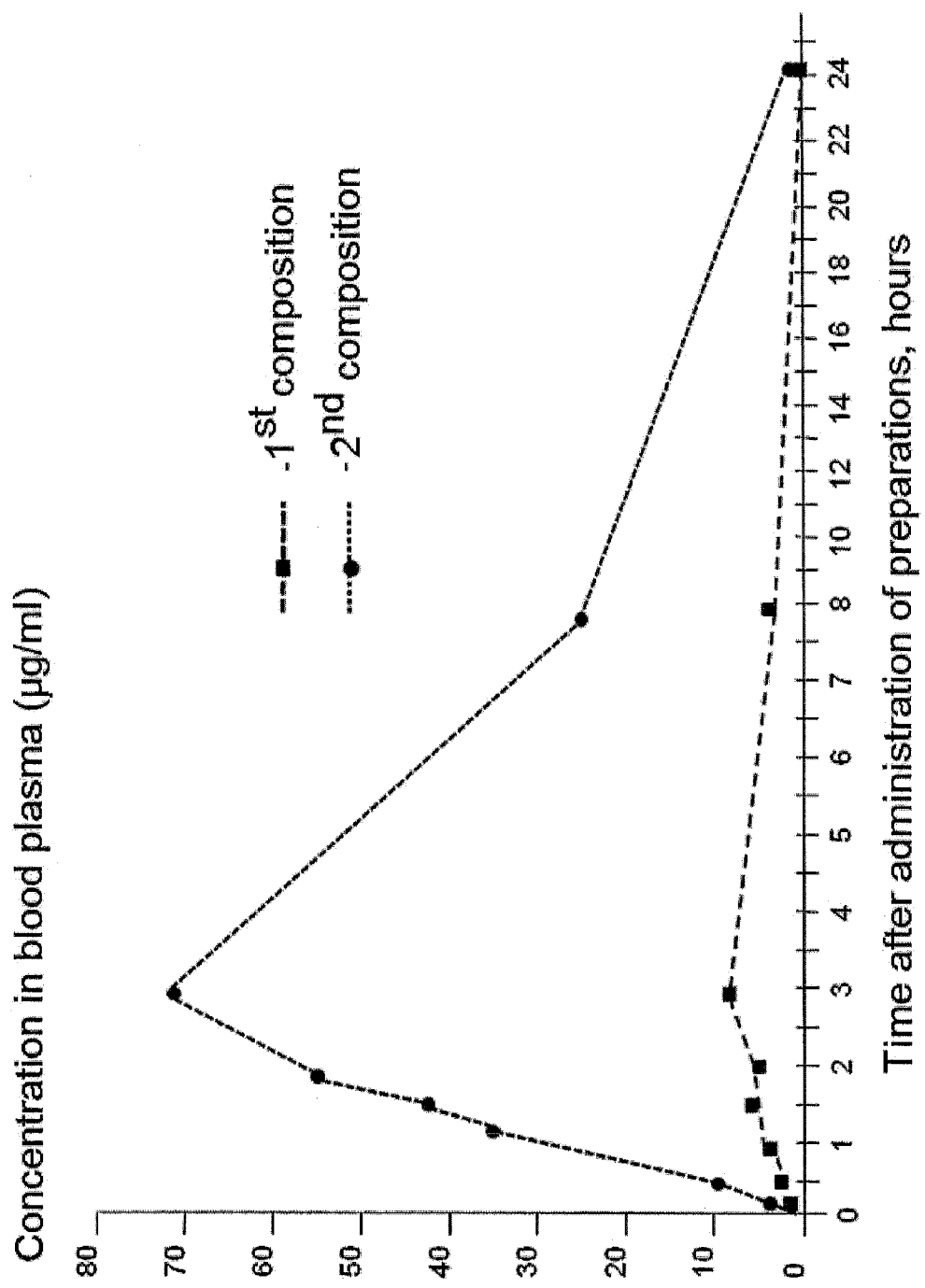
FIG. 1 represents a pharmacokinetic profile of epigallocatechol-3-gallate in the plasma of rats,
Composition 1 is epigallocatechol-3-gallate,
Composition 2 represents a formulation of Example 1.
Figure 2:
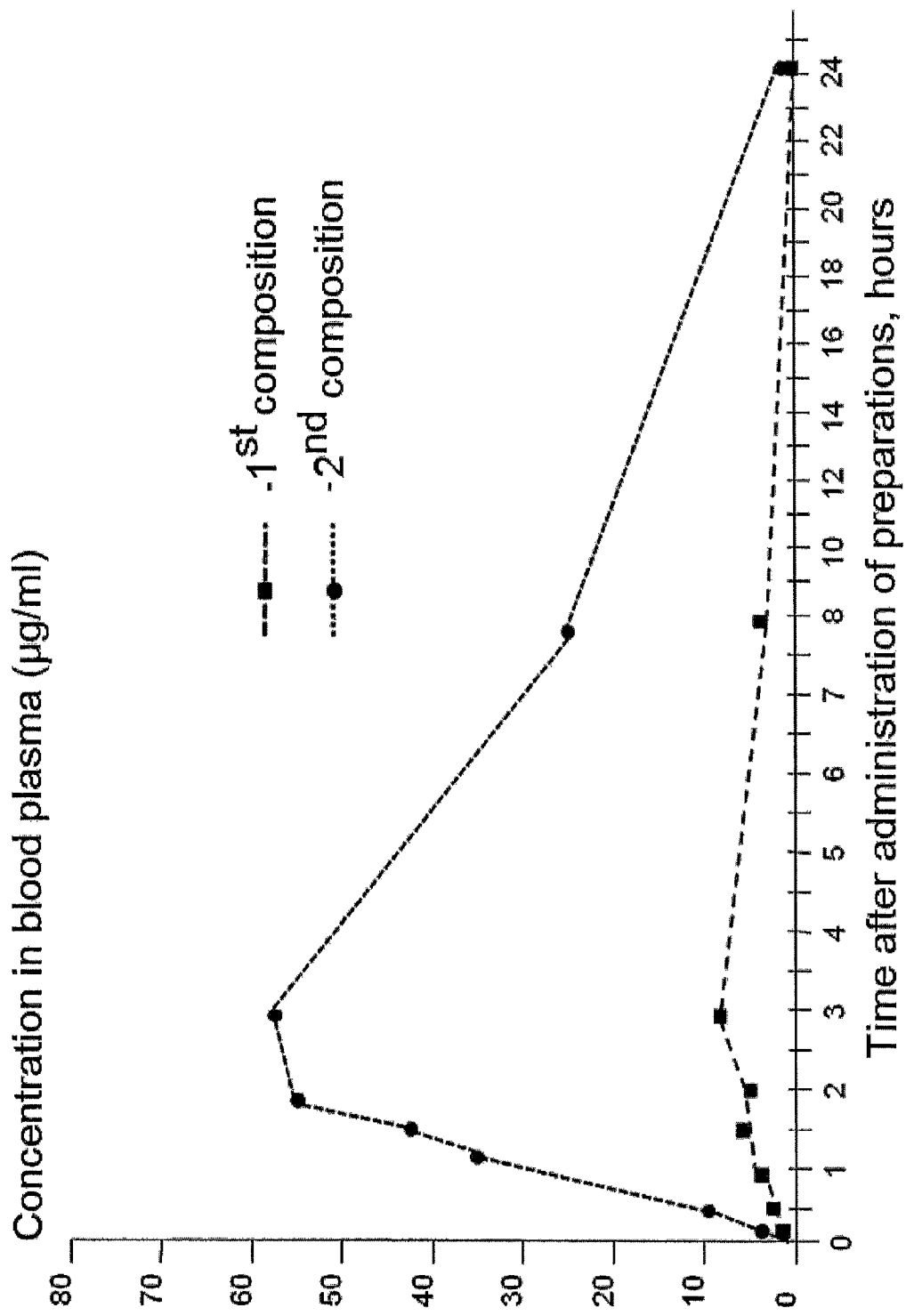
FIG. 2 represents a pharmacokinetic profile of genistein in the plasma of rats,
Composition 1 is genistein,
Composition 2 represents a formulation of Example 2.
Figure 3:
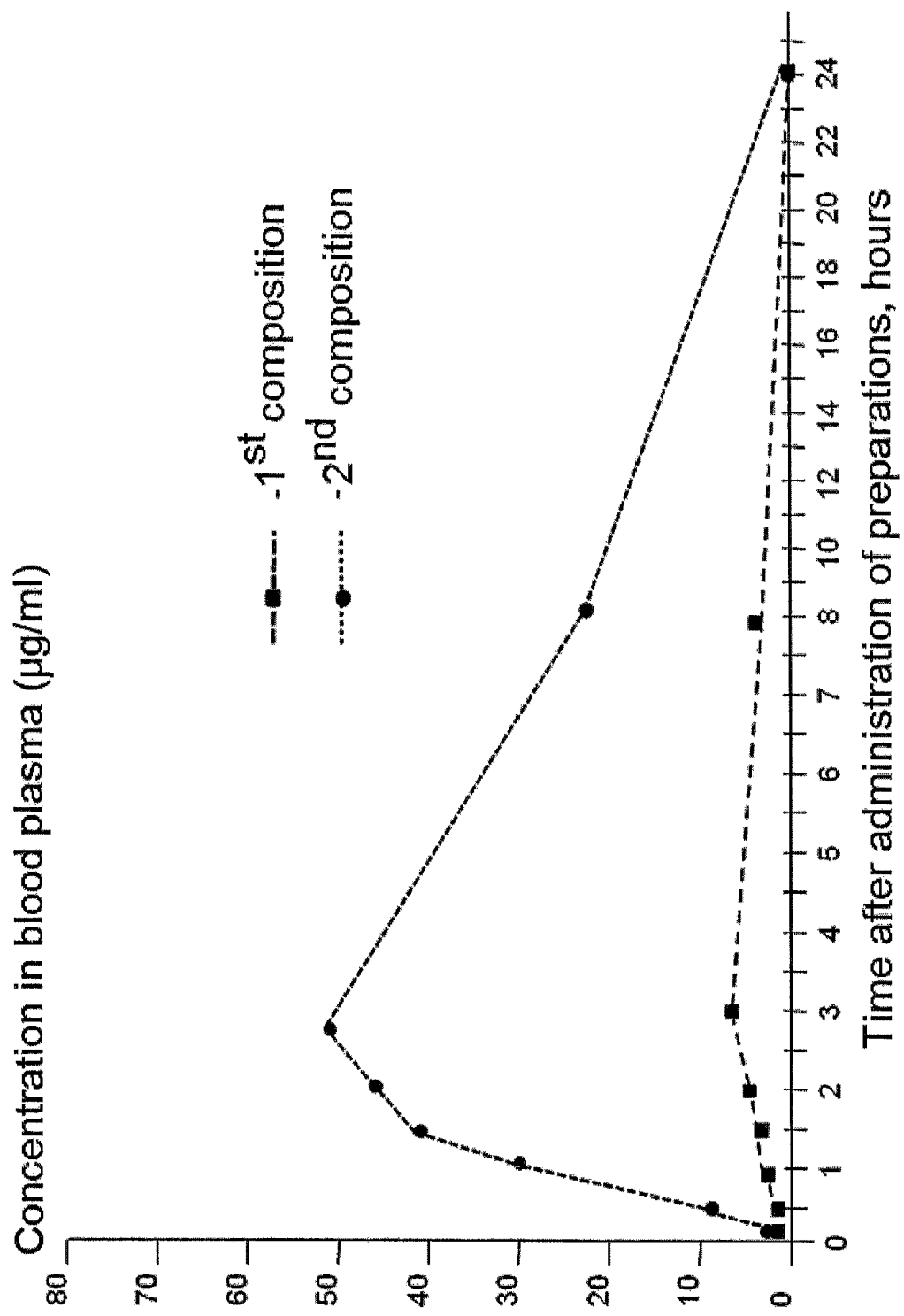
FIG. 3 represents a pharmacokinetic profile of resveratrol in the plasma of rats,
Composition 1 is resveratrol,
Composition 2 represents a formulation of Example 3.
Figure 4:
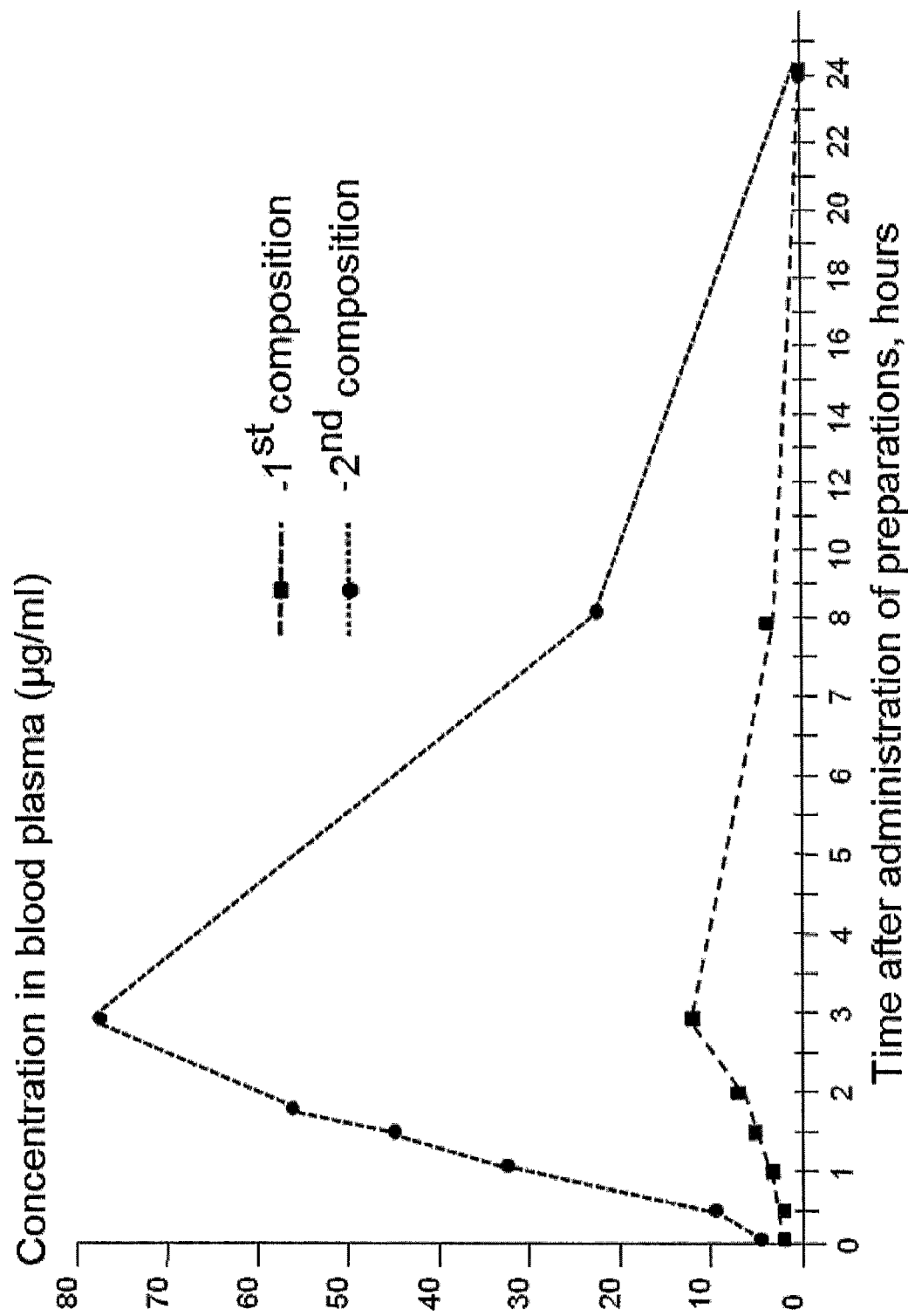
FIG. 4 represents a pharmacokinetic profile of curcumin in the plasma of rats,
Composition 1 is curcumin,
Composition 2 represents a formulation of Example 4.
Figure 5:
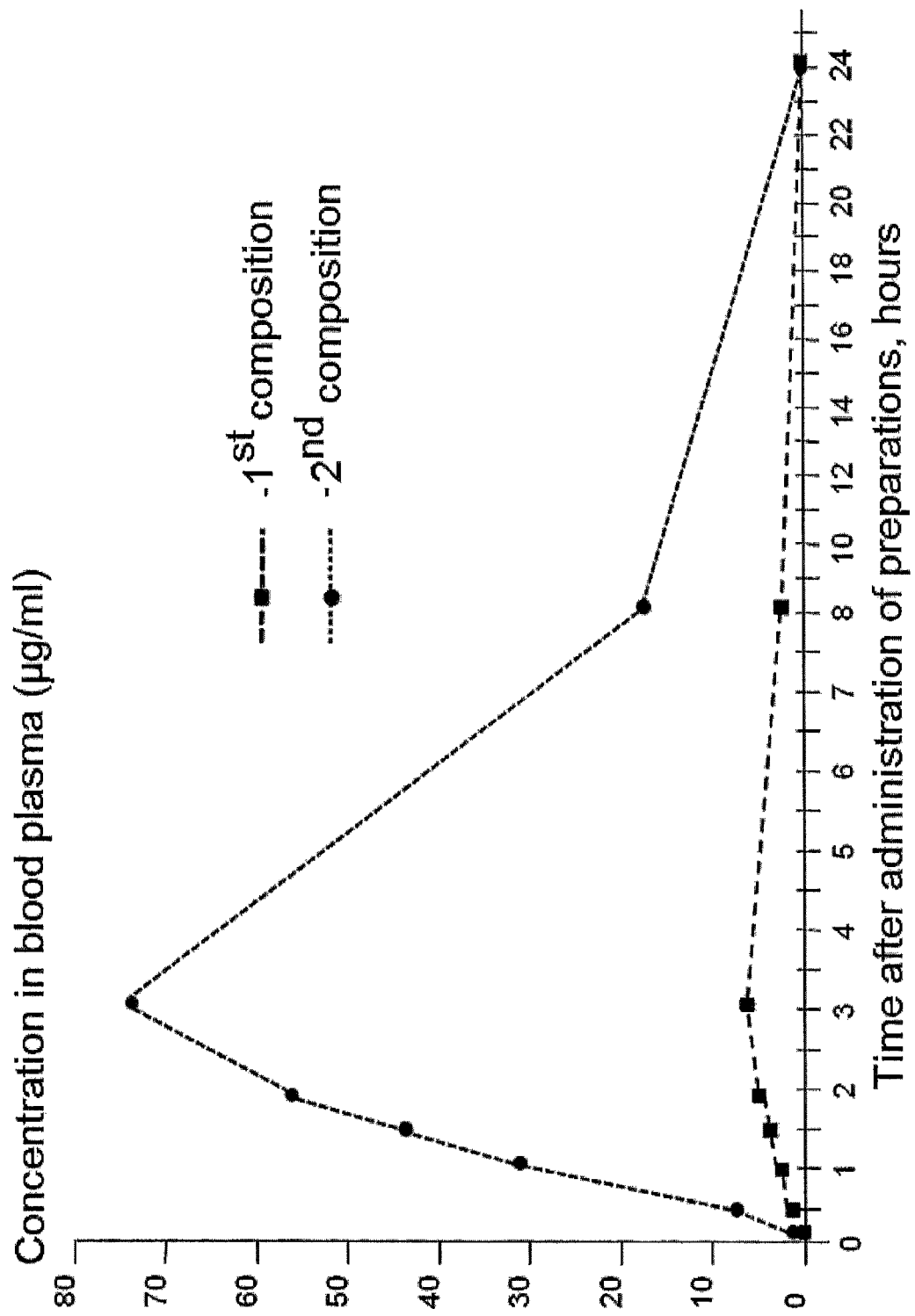
FIG. 5 represents a pharmacokinetic profile of diindolylmethane in the plasma of rats,
Composition 1 is diindolylmethane,
Composition 2 represents a formulation of Example 5.

The present invention is illustrated by the following examples.

EXAMPLE 1

Preparation of the Epigallocatechol-3-Gallate Formulation

A polyvinylcaprolactam/polyvinylacetate/polyethyleneglycol graft copolymer with an average molecular mass of 90000 determined by gel-permeation chromatography in the amount of 5 g is dissolved in 50 ml of ethanol while stirring. A solution of 1 g of epigallocatechol-3-gallate in 20 ml of isopropanol is obtained separately. After that, the solution of epigallocatechin-3-gallate is added to the polymer solution under stirring. The resulting solution is heated to 45° C. under constant stirring and then the solvent is distilled off until dry and the solution is dried in a vacuum-drying box. A slightly colored product is obtained.

EXAMPLE 2

Preparation of the Genistein Formulation 5 g of polyvinylcaprolactam/polyvinylacetate/polyethyleneglycol graft copolymer with an average molecular mass of 140000 determined by gel-permeation chromatography are dissolved in 50 ml of acetone while stirring. A solution of 2 g of genistein in 20 ml of ethanol is obtained separately. After that, the solution of genistein is added to the polymer solution under stirring. The resulting solution is heated to 50° C. under constant stirring and then the solvent is distilled off until dry and the solution is dried in a vacuum-drying box. A slightly colored solid product is obtained.

EXAMPLE 3

Preparation of the Resveratrol Formulation 5 g of polyvinylcaprolactam/polyvinylacetate/polyethyleneglycol graft copolymer 600 with an average molecular mass of 110000 determined by gel-permeation chromatography are dissolved in 50 ml of isopropanol while stirring. A solution of 3 g of resveratrol in 20 ml of ethanol is obtained separately. After that, the solution of resveratrol is added to the polymer solution under stirring. The resulting solution is heated to 45° C. under constant stirring and then the solvent is distilled off until dry and the solution is dried in a vacuum-drying box. A slightly colored solid product is obtained.

EXAMPLE 4

Preparation of the Curcumin Formulation 5 g of polyvinylcaprolactam/polyvinylacetate/polyethyleneglycol graft copolymer with an average molecular mass of 90000 determined by gel-permeation chromatography are dissolved in 50 ml of acetone while stirring. A solution of 4 g of curcumin in 20 ml of ethanol is obtained separately. After that, the solution of curcumin is added to the polymer solution under stirring. The resulting solution is heated to 50° C. under constant stirring and then the solvent is distilled off until dry and the solution is dried in a vacuum-drying box. A slightly colored solid product is obtained.

EXAMPLE 5

Preparation of the Diindolylmethane Formulation 5 g of polyvinylcaprolactam/polyvinylacetate/polyethyleneglycol graft copolymer with an average molecular mass of 140000 determined by gel-permeation chromatography are dissolved in 50 ml of ethanol while stirring. A solution of 5 g of diindolylmethane in 20 ml of ethanol is obtained separately. After that, the solution of diindolylmethane is added to the polymer solution under stirring. The resulting solution is heated to 45° C. under constant stirring and then the solvent is distilled off until dry and the solution is dried in a vacuum-drying box. A slightly colored solid product is obtained.

EXAMPLE 6

Preparation of the Diindolylmethane+Curcumin Formulation 5 g of polyvinylcaprolactam/polyvinylacetate/polyethyleneglycol graft copolymer with an average molecular mass of 140000 determined by gel-permeation chromatography are dissolved in 50 ml of ethanol while stirring. A solution of 3 g of diindolylmethane and of 2 g of curcumin in 20 ml of isopropanol is obtained separately. After that, the solution of phyto-nutrients is added to the polymer solution under stirring. The resulting solution is heated to 45° C. under constant stirring and then the solvent is distilled off until dry and the solution is dried in a vacuum-drying box. A slightly colored solid product is obtained.

EXAMPLE 7

Preparation of the Diindolylmethane+Resveratrol Formulation 5 g of polyvinylcaprolactam/polyvinylacetate/polyethyleneglycol graft copolymer with an average molecular mass of 140000 determined by gel-permeation chromatography are dissolved in 50 ml of ethanol while stirring. A solution of 2 g of diindolylmethane and of 2 g of resveratrol in 20 ml of isopropanol is obtained separately. After that, the solution of phyto-nutrients is added to the polymer solution under stirring. The resulting solution is heated to 45° C. under constant stirring and then the solvent is distilled off until dry and the solution is dried in a vacuum-drying box. A slightly colored solid product is obtained.

EXAMPLE 8

Preparation of the Epigallocatechol-3-Gallate+Genistein Formulation 5 g of polyvinylcaprolactam/polyvinylacetate/polyethyleneglycol graft copolymer with an average molecular mass of 140000 determined by gel-permeation chromatography are dissolved in 50 ml of ethanol while stirring. A solution of 1 g of epigallocatechol-3-gallate and of 2 g of genistein in 20 ml of isopropanol is obtained separately. After that, the solution of phyto-nutrients is added to the polymer solution under stirring. The resulting solution is heated to 45° C. under constant stirring and then the solvent is distilled off until dry and the solution is dried in a vacuum-drying box. A slightly colored solid product is obtained.

EXAMPLE 9

Pharmacokinetic Study of Samples Prepared in Examples 1-6

The experiments used laboratory rats of the Sprague-Dawley family with a weight of 250-350 g. All the studies on the animals have been carried out according to the "Guidelines for Care and Use of Experimental Animals".

Peroral administration of control preparations has been carried out at a dosage of 50 mg/kg. At fixed time intervals (10, 30 min, 1, 1.5, 2, 3, 8 and 24 hours), blood samples were taken at the animals; after centrifugation of said samples, blood plasma was taken for analysis, it was frozen and kept at −80° C. until performing studies.

To carry out analytical studies, the plasma samples were defrosted, centrifuged and separated into aliquot volumes of 0.1 ml. The samples were extracted 3 times in 2 ml of acetone for 5 minutes under permanent shaking. After extraction, the specimens were centrifuged at 1000 rpm for 10 min. The supernatant was separated and put into a glass tube. The organic phase was distilled off and the dried samples were stored at −80° C. until a chromatographic analysis.

The data are graphically shown on drawings representing the pharmacologic profile of phyto-nutrients in the rat plasma (see FIGS. 1-5).

EXAMPLE 10

Study of Anti-Tumor Efficiency of Phyto-Nutrient Preparations Having a Higher Bioavailability in In Vivo Experiments Mice females of the C3H/He line (6-8 weeks) were kept in standard cages in separate rooms at 12 hours/day lighting and at a free access to feed and water. Air temperature in the room was maintained at 20-25° C. for relative humidity of 50-70%. All the manipulations with the laboratory animals were carried out in accordance with the "Guidelines for performing work with the use of experimental animals".

To induce solid tumors, cells of the MBT-2 line (bladder cancer) ($5\times10^5$) in 50 μl of phosphate buffer were injected subcutaneously to the animals, into the right dorsal lateral area, and after that, 4 times a week, the animal body mass, the feed consumption and the tumor size were measured. The tumor size was calculated according to the formula:

$$V = \pi/6 \times L(\text{mm}) \times W^2 (\text{mm}^2),$$

where L is the long size and W is the short size of the tumor.

Figure 6:
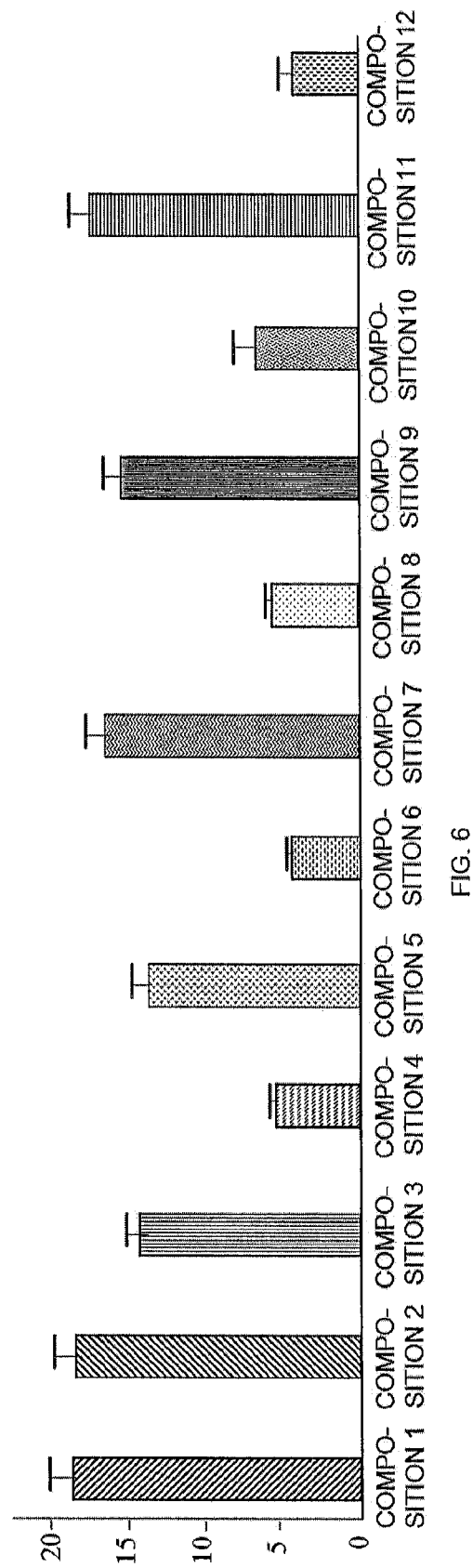
FIG. 6 represents the results of studies of the phyto-nutrient anti-tumor activity in vivo experiments.
Composition 1 is a control,
Composition 2 is a control: Soluplus®,
Composition 3 is diindolylmethane,
Composition 4 represents a formulation of Example 3,
Composition 5 is epigallocatechol-3-gallate,
Composition 6 represents a formulation of Example 1,
Composition 7 is curcumin,
Composition 8 represents a formulation of Example 4,
Composition 9 is resveratrol,
Composition 10 represents a formulation of Example 3,
Composition 11 is genistein,
Composition 12 represents a formulation of Example 2.

In experiments for the study of the curative anti-tumor effect of phyto-nutrients, the compounds under study were started to inject on day 15 (14 days later) after implanting tumor cells into animals with a palpable tumor (a node). The final size of the tumor was evaluated on day 29 of the experiment: the animals were killed (under ethereal narcosis), the tumors were dissected away and weighted. As shown on a drawing (see FIG. 6), the phyto-nutrient preparations under study, based on a matrix draft polymer, show a marked anti-tumor effect. In the experimental group of animals that received initial substances orally at the rate of daily 10 mg, the average size of the tumor represented 80% of that of the control, while in mice receiving phyto-nutrients with a higher bioavailability at the rate of daily 10 mg, the average tumor-volume was less than 30% of that of the control.

The data obtained bears a convincing witness of a significant increase of the anti-tumor effect of the substances under study compared to the anti-tumor effect of the base prior art products. It is obvious that the considerable increase of the tumor-suppressing activity of phyto-nutrients is due to a higher bioavailability of the active substances.

In this way, these preparations show a significant anti-tumor effect against experimental tumors of a bladder on an animal model in vivo.

A histological study of a tumor tissue of animals that received the preparations under study showed that said preparations in applied dosages did not induce any modifications of the cellular morphology in the liver, kidney or other functionally important organs, they neither have effect on the weight of experimental animals.

EXAMPLE 11

Study of the Anti-Tumor Efficiency of a Combined Preparation Containing Diindolylmethane and Curcumin of Example 6

Figure 7:
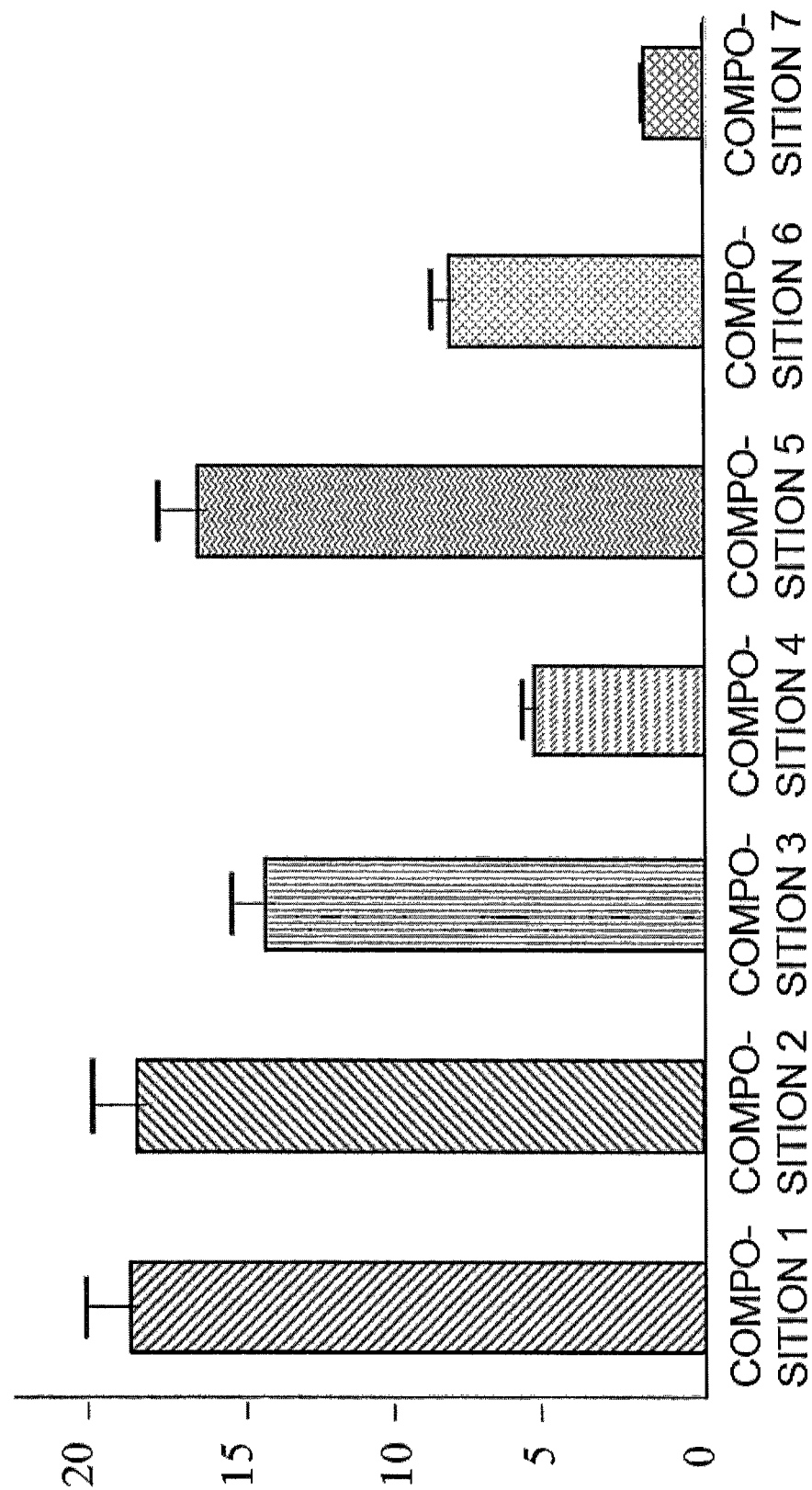
FIG. 7 represents the results of studies of the anti-tumor activity for a combined preparation (diindolylmethane and curcumin).
Composition 1 is a control,
Composition 2 is a control: Soluplus®,
Composition 3 is diindolylmethane,
Composition 4 represents a formulation of Example 5,
Composition 5 is curcumin,
Composition 6 represents a formulation of Example 4,
Composition 7 represents a formulation of Example 6.

In the experiments studying the curative anti-tumor effect of a combined preparation, the preparation under study was administered orally on day 15 (after 14 days) following the day of implanting tumor cells to animals with a palpable tumor (a node). The final size of the tumor was evaluated on day 29 of the experiment. The combined preparation was prepared by simple mixing of specimens obtained in Examples 4 and 5. The mice received totally daily 5 mg of every preparation from these Examples. The data obtained is represented in a drawing (see FIG. 7). The results obtained bear a convincing witness of a significant increase of the anti-tumor effect of the combination of substances compared to the anti-tumor effect of the base prior art products, as well as compared to the preparations delivered separately. It is obvious that the considerable increase of the tumor-suppressing activity of diindolylmethane and curcumin is due to a synergetic effect of the combination of two substances and to a higher bioavailability of the active substances.

EXAMPLE 12

Study of the Anti-Tumor Efficiency of a Combined Preparation Containing Diindolylmethane and Resveratrol of Example 6

Figure 8:
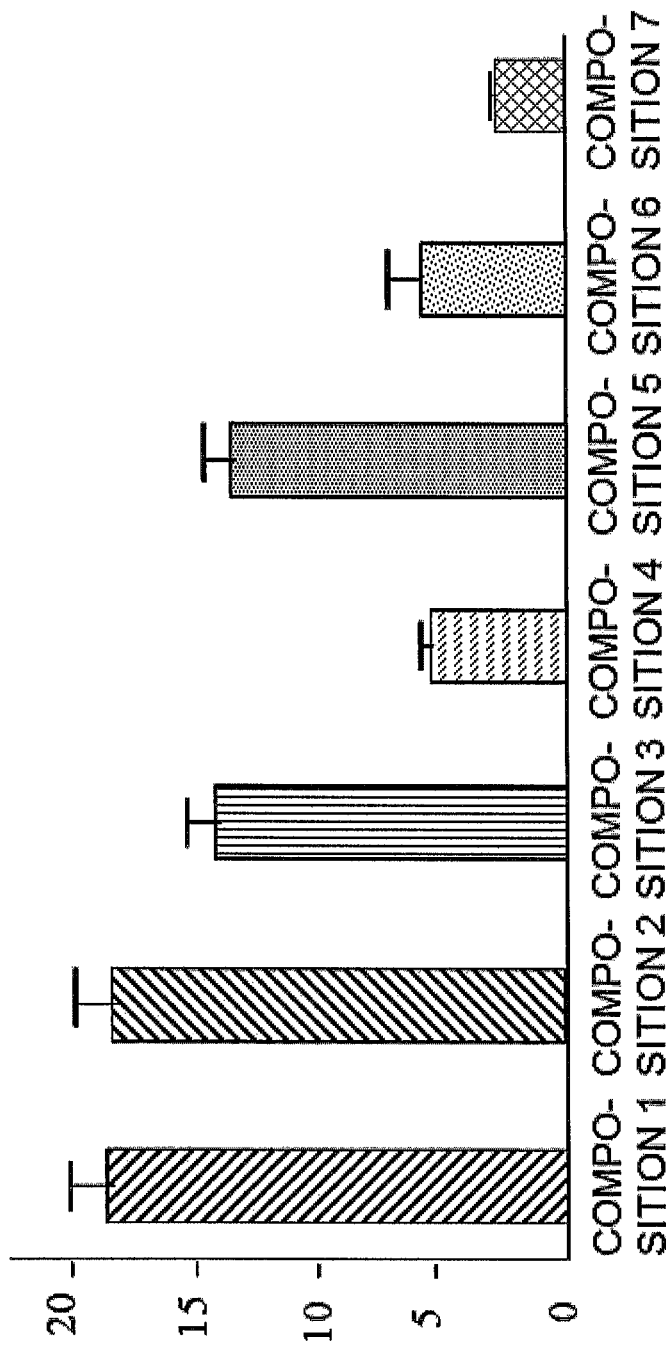
FIG. 8 represents the results of studies of the anti-tumor activity for a combined preparation (diindolylmethane and resveratrol).
Composition 1 is a control,
Composition 2 is a control: Soluplus®,
Composition 3 is diindolylmethane,
Composition 4 represents a formulation of Example 5,
Composition 5 is resveratrol,
Composition 6 represents a formulation of Example 3,
Composition 7 represents a formulation of Example 7.

The experiments were carried out in a similar way to those of Example 11, the results are given in FIG. 8. The results obtained bear a convincing witness of a significant increase of the anti-tumor effect of the combination of substances compared to the anti-tumor effect of the base prior art products, as well as compared to the preparations delivered separately. It is obvious that the considerable increase of the tumor-suppressing activity of diindolylmethane and resveratrol is due to a synergetic effect of the combination of two substances and to a higher bioavailability of the active substances.

EXAMPLE 13

Study of the Anti-Tumor Efficiency of a Combined Preparation Containing Epigallocatechol-3-Gallate and Genistein of Example 8

Figure 9:
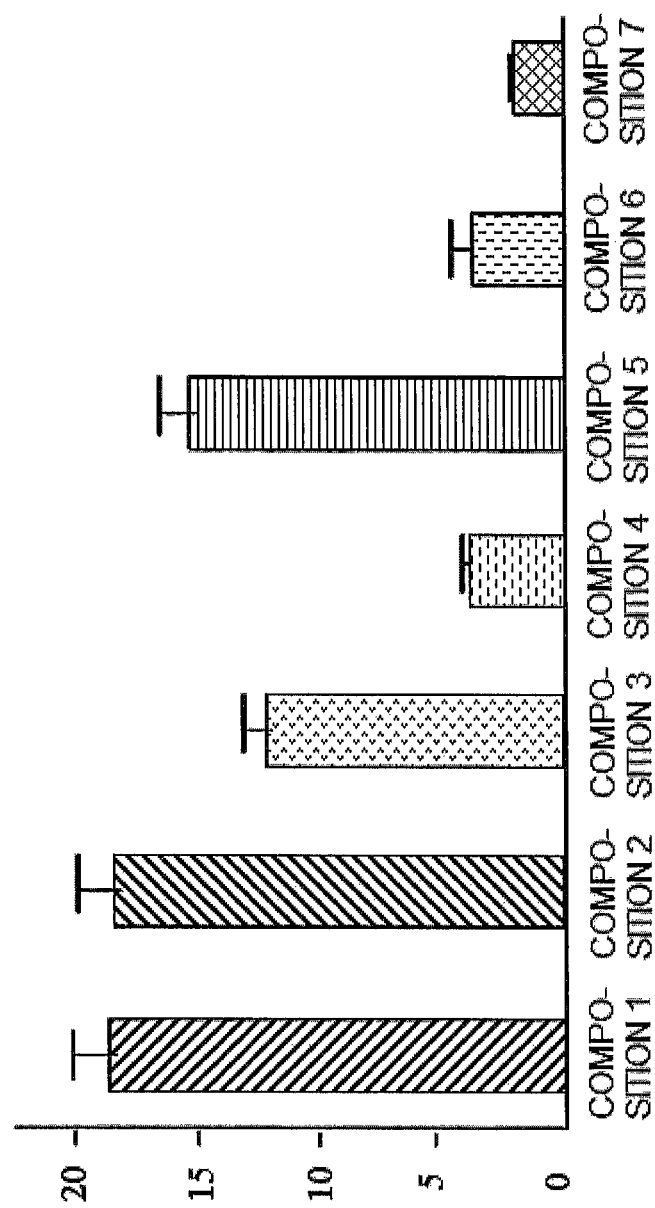
FIG. 9 represents the results of studies of the anti-tumor activity for a combined preparation (epigallocatechin-3-gallate and genistein).
Composition 1 is a control,
Composition 2 is a control: Soluplus®,
Composition 3 is epigallocatechin-3-gallate,
Composition 4 represents a formulation of Example 1,
Composition 5 is genistein,
Composition 6 represents a formulation of Example 2,
Composition 7 represents a formulation of Example 8.

The experiments were carried out in a similar way to those of Example 11, the results are given in FIG. 9. The results obtained bear a convincing witness of a significant increase of the anti-tumor effect of the combination of substances compared to the anti-tumor effect of the base prior art products, as well as compared to the preparations delivered separately. It is obvious that the considerable increase of the tumor-suppressing activity of epigallocatechol-3-gallate and of genistein is due to a synergetic effect of the combination of two substances and to a higher bioavailability of the active substances.

EXAMPLE 14

Preparation of a Phyto-Nutrient Formulation by a Method of Dry Mixing

A polyvinylcaprolactam/polyvinylacetate/polyethyleneglycol graft copolymer with an average molecular mass of 90000 determined by gel-permeation chromatography in the amount of 10 g is mixed with 1.5-10 g of phyto-nutrient selected from the following series: epigallocatechol-3-gallate, diindolylmethane, genistein, resveratrol, curcumin. The resulting dry mixture was thoroughly stirred in a mixer to obtain a homogenous powder. The powder obtained was used in pharmacokinetic studies.

The following Table comprises data of phyto-nutrient bioavailability while producing a composition of the present invention by dry mixing.

TABLE

| No | Phyto-nutrient | Improvement of Bioavailability |
|---|---|---|
| 1 | Epigallocatechol-3-gallate | 2.8 times |
| 2 | Diindolylmethane | 3.7 times |
| 3 | Resveratrol | 3.2 times |
| 4 | Genistein | 2.9 times |
| 5 | Curcumin | 3.1 times |

The invention claimed is:

1. Method for producing a pharmaceutical composition for peroral administration, wherein the solubilizer is dissolved in an organic solvent, at least one phyto-nutrient is dissolved in the same organic solvent, the resulting solutions are mixed and the solvent is distilled off in vacuum, wherein the use is made of at least one phyto-nutrient selected from the following series: epigallocatechol-3-gallate, diindolylmethane, genistein, resveratrol and curcumin; as the solubilizer, use is made of a polyvinylcaprolactam/polyvinylacetate/polyethyleneglycol graft copolymer with an average molecular mass of 90000-140000 g/mol, at a mass ratio of at least one phyto-nutrient and of the solubilizer of 1:1 to 1:5; after the solutions are mixed, the resulting mixture is heated to 45-50° C. with constant stirring and, after distillation, the product is dried in vacuum.

2. Method of claim 1, wherein, as an organic solvent, use is made of ethanol or acetone, or isopropanol.

3. Method of claim 1, wherein after drying, a pharmaceutically acceptable carrier is added to the product.

* * * * *